(12) United States Patent
White et al.

(10) Patent No.: US 8,486,150 B2
(45) Date of Patent: Jul. 16, 2013

(54) PATIENT-MODIFIED IMPLANT

(75) Inventors: John R. White, Winona Lake, IN (US);
Robert Metzger, Wakarusa, IN (US);
Keith R. Berend, Columbus, OH (US)

(73) Assignee: Biomet Manufacturing Corp., Warsaw, IN (US)

( * ) Notice: Subject to any disclaimer, the term of this patent is extended or adjusted under 35 U.S.C. 154(b) by 0 days.

(21) Appl. No.: 13/081,618

(22) Filed: Apr. 7, 2011

(65) Prior Publication Data
US 2011/0184526 A1    Jul. 28, 2011

Related U.S. Application Data

(62) Division of application No. 12/103,834, filed on Apr. 16, 2008, now Pat. No. 7,967,868.

(60) Provisional application No. 60/912,178, filed on Apr. 17, 2007.

(51) Int. Cl.
*A61F 2/38* (2006.01)
(52) U.S. Cl.
USPC ............... 623/20.21; 623/20.32; 623/20.14
(58) Field of Classification Search
CPC .......................................................... A61F 2/38
USPC ............... 623/20.14–20.21, 20.32–20.35
IPC .......................................................... A61F 2/38
See application file for complete search history.

(56) References Cited

U.S. PATENT DOCUMENTS

| | | | |
|---|---|---|---|
| 1,480,285 | A | 1/1924 | Moore |
| 2,407,845 | A | 9/1946 | Nemeyer |
| 2,618,913 | A | 11/1952 | Plancon et al. |
| 2,910,978 | A | 11/1959 | Urist |
| 3,840,904 | A | 10/1974 | Tronzo |
| 4,306,866 | A | 12/1981 | Weissman |
| 4,324,006 | A | 4/1982 | Charnley |
| 4,421,112 | A | 12/1983 | Mains et al. |
| 4,436,684 | A | 3/1984 | White |
| 4,475,549 | A | 10/1984 | Oh |
| 4,506,393 | A | 3/1985 | Murphy |
| 4,528,980 | A | 7/1985 | Kenna |

(Continued)

FOREIGN PATENT DOCUMENTS

| CA | 2447694 A1 | 12/2002 |
|---|---|---|
| CA | 2501041 A1 | 4/2004 |

(Continued)

OTHER PUBLICATIONS

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

(Continued)

*Primary Examiner* — Thomas Sweet
*Assistant Examiner* — Jason-Dennis Stewart
(74) *Attorney, Agent, or Firm* — Harness, Dickey

(57) ABSTRACT

An orthopedic implant includes a first portion including at least one feature modified to be patient-specific and match the anatomy of a specific patient from a three-dimensional digital image of a patient's joint using computer modeling. The orthopedic implant includes a non-custom inner bone-engaging surface including a plurality of planar surfaces configured for engagement with non-custom bone cuts.

20 Claims, 4 Drawing Sheets

U.S. PATENT DOCUMENTS

| | | |
|---|---|---|
| 4,619,658 A | 10/1986 | Pappas et al. |
| 4,621,630 A | 11/1986 | Kenna |
| 4,632,111 A | 12/1986 | Roche |
| 4,663,720 A | 5/1987 | Duret et al. |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,721,104 A | 1/1988 | Kaufman et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,893,619 A | 1/1990 | Dale et al. |
| 4,896,663 A | 1/1990 | Vandewalls |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,007,936 A | 4/1991 | Woolson |
| 5,030,221 A | 7/1991 | Buechel et al. |
| 5,041,117 A | 8/1991 | Engelhardt |
| 5,053,039 A | 10/1991 | Hofmann et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,246,444 A | 9/1993 | Schreiber |
| 5,258,032 A | 11/1993 | Bertin |
| 5,261,915 A | 11/1993 | Durlacher et al. |
| 5,274,565 A | 12/1993 | Reuben |
| 5,299,288 A | 3/1994 | Glassman et al. |
| 5,300,077 A | 4/1994 | Howell |
| 5,320,625 A | 6/1994 | Bertin |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,527,317 A | 6/1996 | Ashby et al. |
| 5,539,649 A | 7/1996 | Walsh et al. |
| 5,540,695 A | 7/1996 | Levy |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,595,703 A | 1/1997 | Swaelens et al. |
| 5,607,431 A | 3/1997 | Dudasik et al. |
| 5,613,969 A | 3/1997 | Jenkins, Jr. |
| 5,620,448 A | 4/1997 | Puddu |
| 5,634,927 A | 6/1997 | Houston et al. |
| 5,658,294 A | 8/1997 | Sederholm |
| 5,662,656 A | 9/1997 | White |
| 5,677,107 A | 10/1997 | Neckers |
| 5,681,354 A | 10/1997 | Eckhoff |
| 5,682,886 A | 11/1997 | Delp et al. |
| 5,690,635 A | 11/1997 | Matsen, III et al. |
| 5,697,933 A | 12/1997 | Gundlapalli et al. |
| 5,702,460 A | 12/1997 | Carls et al. |
| 5,704,941 A | 1/1998 | Jacober et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,768,134 A | 6/1998 | Swaelens et al. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,033,415 A | 3/2000 | Mittelstadt et al. |
| 6,056,754 A | 5/2000 | Haines et al. |
| 6,059,789 A | 5/2000 | Dinger et al. |
| 6,059,833 A | 5/2000 | Doets |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,254,604 B1 | 7/2001 | Howell |
| 6,258,097 B1 | 7/2001 | Cook et al. |
| 6,264,698 B1 | 7/2001 | Lawes et al. |
| 6,273,891 B1 | 8/2001 | Masini |
| 6,290,727 B1 | 9/2001 | Otto et al. |
| 6,293,971 B1 | 9/2001 | Nelson et al. |
| 6,312,473 B1 | 11/2001 | Oshida |
| 6,319,285 B1 | 11/2001 | Chamier et al. |
| 6,325,829 B1 | 12/2001 | Schmotzer |
| 6,338,738 B1 | 1/2002 | Bellotti et al. |
| 6,343,987 B2 | 2/2002 | Hayama et al. |
| 6,354,011 B1 | 3/2002 | Albrecht |
| 6,383,228 B1 | 5/2002 | Schmotzer |
| 6,391,251 B1 | 5/2002 | Keicher et al. |
| 6,395,005 B1 | 5/2002 | Lovell |
| 6,427,698 B1 | 8/2002 | Yoon |

| | | |
|---|---|---|
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,990,220 B2 | 1/2006 | Ellis et al. |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,141,053 B2 | 11/2006 | Rosa et al. |
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma de La Barrera |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,527,631 B2 | 5/2009 | Maroney et al. |
| 7,534,263 B2 | 5/2009 | Burdulis, Jr. et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,704,253 B2 | 4/2010 | Bastian et al. |
| 7,723,395 B2 | 5/2010 | Ringeisen et al. |
| 7,780,740 B2 | 8/2010 | Steinberg |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,819,925 B2 | 10/2010 | King et al. |
| 7,828,806 B2 | 11/2010 | Graf et al. |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 8,062,301 B2 | 11/2011 | Ammann et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,133,230 B2 | 3/2012 | Stevens et al. |
| 8,137,406 B2 | 3/2012 | Novak et al. |
| 8,182,489 B2 | 5/2012 | Horacek |
| 8,192,441 B2 | 6/2012 | Collazo |
| 8,241,292 B2 | 8/2012 | Collazo |
| 8,303,596 B2 | 11/2012 | Plaßky et al. |
| 2001/0005797 A1 | 6/2001 | Barlow et al. |
| 2001/0011190 A1 | 8/2001 | Park |
| 2001/0054478 A1 | 12/2001 | Watanabe et al. |
| 2002/0007294 A1 | 1/2002 | Bradbury et al. |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 | 8/2002 | Picard et al. |
| 2002/0147415 A1 | 10/2002 | Martelli |

| | | |
|---|---|---|
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1* | 7/2003 | Tuke et al. ................. 623/20.32 |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0149283 A1 | 7/2006 | May et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0190086 A1 | 8/2006 | Clemow et al. |
| 2006/0195111 A1 | 8/2006 | Couture |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |

| | | | | | | |
|---|---|---|---|---|---|---|
| 2007/0233140 A1 | 10/2007 | Metzger et al. | | 2009/0018666 A1 | 1/2009 | Grundei et al. |
| 2007/0233141 A1 | 10/2007 | Park et al. | | 2009/0024131 A1 | 1/2009 | Metzger et al. |
| 2007/0233269 A1 | 10/2007 | Steines et al. | | 2009/0043556 A1 | 2/2009 | Axelson et al. |
| 2007/0233272 A1 | 10/2007 | Boyce et al. | | 2009/0076371 A1 | 3/2009 | Lang et al. |
| 2007/0238069 A1 | 10/2007 | Lovald et al. | | 2009/0076512 A1 | 3/2009 | Ammann et al. |
| 2007/0239282 A1 | 10/2007 | Caylor et al. | | 2009/0076520 A1 | 3/2009 | Choi |
| 2007/0239481 A1 | 10/2007 | DiSilvestro et al. | | 2009/0082770 A1 | 3/2009 | Worner et al. |
| 2007/0250169 A1 | 10/2007 | Lang | | 2009/0082774 A1 | 3/2009 | Oti et al. |
| 2007/0253617 A1 | 11/2007 | Arata et al. | | 2009/0087276 A1 | 4/2009 | Rose |
| 2007/0255288 A1 | 11/2007 | Mahfouz et al. | | 2009/0088674 A1 | 4/2009 | Caillouette et al. |
| 2007/0255412 A1 | 11/2007 | Hajaj et al. | | 2009/0088753 A1 | 4/2009 | Aram et al. |
| 2007/0262867 A1 | 11/2007 | Westrick et al. | | 2009/0088754 A1 | 4/2009 | Aker et al. |
| 2007/0276224 A1 | 11/2007 | Lang et al. | | 2009/0088755 A1 | 4/2009 | Aker et al. |
| 2007/0276400 A1 | 11/2007 | Moore et al. | | 2009/0088758 A1 | 4/2009 | Bennett |
| 2007/0276501 A1 | 11/2007 | Betz et al. | | 2009/0088759 A1 | 4/2009 | Aram et al. |
| 2007/0288029 A1 | 12/2007 | Justin et al. | | 2009/0088760 A1 | 4/2009 | Aram et al. |
| 2007/0288030 A1 | 12/2007 | Metzger et al. | | 2009/0088761 A1 | 4/2009 | Roose et al. |
| 2008/0009952 A1 | 1/2008 | Hodge | | 2009/0088763 A1 | 4/2009 | Aram et al. |
| 2008/0015599 A1 | 1/2008 | D'Alessio et al. | | 2009/0088865 A1 | 4/2009 | Brehm |
| 2008/0015603 A1 | 1/2008 | Collazo | | 2009/0088866 A1 | 4/2009 | Case |
| 2008/0015604 A1 | 1/2008 | Collazo | | 2009/0089034 A1 | 4/2009 | Penney et al. |
| 2008/0015605 A1 | 1/2008 | Collazo | | 2009/0089081 A1 | 4/2009 | Haddad |
| 2008/0021299 A1 | 1/2008 | Meulink | | 2009/0093815 A1 | 4/2009 | Fletcher et al. |
| 2008/0021494 A1 | 1/2008 | Schmelzeisen-Redeker et al. | | 2009/0093816 A1 | 4/2009 | Roose et al. |
| 2008/0021567 A1 | 1/2008 | Meulink et al. | | 2009/0096613 A1 | 4/2009 | Westrick |
| 2008/0027563 A1 | 1/2008 | Johnson et al. | | 2009/0099567 A1 | 4/2009 | Zajac |
| 2008/0039850 A1 | 2/2008 | Rowley et al. | | 2009/0105837 A1 | 4/2009 | Lafosse et al. |
| 2008/0051799 A1 | 2/2008 | Bonutti | | 2009/0118736 A1 | 5/2009 | Kreuzer |
| 2008/0051910 A1 | 2/2008 | Kammerzell et al. | | 2009/0118769 A1 | 5/2009 | Sixto, Jr. et al. |
| 2008/0058945 A1 | 3/2008 | Hajaj et al. | | 2009/0131941 A1 | 5/2009 | Park et al. |
| 2008/0058947 A1 | 3/2008 | Earl et al. | | 2009/0131942 A1 | 5/2009 | Aker et al. |
| 2008/0062183 A1 | 3/2008 | Swaelens | | 2009/0138020 A1 | 5/2009 | Park et al. |
| 2008/0065225 A1 | 3/2008 | Wasielewski et al. | | 2009/0149965 A1 | 6/2009 | Quaid |
| 2008/0097451 A1 | 4/2008 | Chen et al. | | 2009/0149977 A1 | 6/2009 | Schendel |
| 2008/0112996 A1 | 5/2008 | Harlow et al. | | 2009/0151736 A1 | 6/2009 | Belcher et al. |
| 2008/0114370 A1 | 5/2008 | Schoenefeld | | 2009/0157083 A1 | 6/2009 | Park et al. |
| 2008/0133022 A1 | 6/2008 | Caylor | | 2009/0163922 A1 | 6/2009 | Meridew et al. |
| 2008/0140081 A1 | 6/2008 | Heavener et al. | | 2009/0163923 A1 | 6/2009 | Flett et al. |
| 2008/0140209 A1 | 6/2008 | Iannotti et al. | | 2009/0164024 A1 | 6/2009 | Rudan et al. |
| 2008/0140213 A1 | 6/2008 | Ammann et al. | | 2009/0177282 A1 | 7/2009 | Bureau et al. |
| 2008/0146969 A1 | 6/2008 | Kurtz | | 2009/0187193 A1 | 7/2009 | Maroney et al. |
| 2008/0147072 A1 | 6/2008 | Park et al. | | 2009/0209884 A1 | 8/2009 | Van Vorhis et al. |
| 2008/0147073 A1 | 6/2008 | Ammann et al. | | 2009/0209961 A1 | 8/2009 | Ferrante et al. |
| 2008/0161815 A1 | 7/2008 | Schoenefeld et al. | | 2009/0222014 A1 | 9/2009 | Bojarski et al. |
| 2008/0172125 A1 | 7/2008 | Ek | | 2009/0222015 A1 | 9/2009 | Park et al. |
| 2008/0195099 A1 | 8/2008 | Minas | | 2009/0222016 A1 | 9/2009 | Park et al. |
| 2008/0195107 A1 | 8/2008 | Cuckler et al. | | 2009/0222103 A1 | 9/2009 | Fitz et al. |
| 2008/0195108 A1* | 8/2008 | Bhatnagar et al. ............... 606/87 | | 2009/0228016 A1 | 9/2009 | Alvarez |
| 2008/0195216 A1 | 8/2008 | Philipp | | 2009/0234360 A1 | 9/2009 | Alexander |
| 2008/0200926 A1 | 8/2008 | Verard et al. | | 2009/0248044 A1 | 10/2009 | Amiot et al. |
| 2008/0208200 A1 | 8/2008 | Crofford | | 2009/0254093 A1 | 10/2009 | White et al. |
| 2008/0208353 A1 | 8/2008 | Kumar et al. | | 2009/0254367 A1 | 10/2009 | Belcher et al. |
| 2008/0215059 A1 | 9/2008 | Carignan et al. | | 2009/0270868 A1 | 10/2009 | Park et al. |
| 2008/0230422 A1 | 9/2008 | Pleil et al. | | 2009/0274350 A1 | 11/2009 | Pavlovskaia et al. |
| 2008/0234664 A1 | 9/2008 | May et al. | | 2009/0287217 A1 | 11/2009 | Ammann et al. |
| 2008/0234683 A1 | 9/2008 | May | | 2009/0306676 A1 | 12/2009 | Lang et al. |
| 2008/0234685 A1 | 9/2008 | Gjerde | | 2009/0307893 A1 | 12/2009 | Burdulis, Jr. et al. |
| 2008/0234833 A1 | 9/2008 | Bandoh et al. | | 2009/0318836 A1 | 12/2009 | Stone et al. |
| 2008/0243127 A1 | 10/2008 | Lang et al. | | 2009/0318921 A1 | 12/2009 | White et al. |
| 2008/0255674 A1 | 10/2008 | Rahaman et al. | | 2010/0010493 A1 | 1/2010 | Dower |
| 2008/0257363 A1 | 10/2008 | Schoenefeld et al. | | 2010/0016984 A1 | 1/2010 | Trabish |
| 2008/0262500 A1 | 10/2008 | Collazo | | 2010/0016986 A1 | 1/2010 | Trabish |
| 2008/0262624 A1 | 10/2008 | White et al. | | 2010/0023015 A1 | 1/2010 | Park |
| 2008/0269906 A1 | 10/2008 | Iannotti et al. | | 2010/0030231 A1 | 2/2010 | Revie et al. |
| 2008/0275452 A1 | 11/2008 | Lang et al. | | 2010/0042105 A1 | 2/2010 | Park et al. |
| 2008/0281328 A1 | 11/2008 | Lang et al. | | 2010/0049195 A1 | 2/2010 | Park et al. |
| 2008/0281329 A1 | 11/2008 | Fitz et al. | | 2010/0057088 A1 | 3/2010 | Shah |
| 2008/0281426 A1 | 11/2008 | Fitz et al. | | 2010/0076439 A1 | 3/2010 | Hatch |
| 2008/0287926 A1 | 11/2008 | Abou El Kheir | | 2010/0076505 A1 | 3/2010 | Borja |
| 2008/0287954 A1 | 11/2008 | Kunz et al. | | 2010/0076563 A1 | 3/2010 | Otto et al. |
| 2008/0294170 A1 | 11/2008 | O'Brien | | 2010/0076571 A1 | 3/2010 | Hatch |
| 2008/0294266 A1 | 11/2008 | Steinberg | | 2010/0082034 A1 | 4/2010 | Remia |
| 2008/0300600 A1 | 12/2008 | Guelat et al. | | 2010/0082035 A1 | 4/2010 | Keefer |
| 2008/0306485 A1 | 12/2008 | Coon et al. | | 2010/0087829 A1 | 4/2010 | Metzger et al. |
| 2008/0306558 A1 | 12/2008 | Hakki | | 2010/0094295 A1 | 4/2010 | Schnieders et al. |
| 2008/0312659 A1 | 12/2008 | Metzger et al. | | 2010/0105011 A1 | 4/2010 | Karkar et al. |
| 2008/0319448 A1 | 12/2008 | Lavallee et al. | | 2010/0121334 A1 | 5/2010 | Couture et al. |
| 2009/0012526 A1 | 1/2009 | Fletcher | | 2010/0121335 A1 | 5/2010 | Penenberg et al. |
| 2009/0018546 A1 | 1/2009 | Daley | | 2010/0137869 A1 | 6/2010 | Borja et al. |

| | | | |
|---|---|---|---|
| 2010/0137924 A1 | 6/2010 | Tuke et al. | |
| 2010/0145343 A1 | 6/2010 | Johnson et al. | |
| 2010/0145344 A1 | 6/2010 | Jordan et al. | |
| 2010/0152782 A1 | 6/2010 | Stone et al. | |
| 2010/0160917 A1 | 6/2010 | Fitz et al. | |
| 2010/0168752 A1 | 7/2010 | Edwards | |
| 2010/0168754 A1 | 7/2010 | Fitz et al. | |
| 2010/0168857 A1 | 7/2010 | Hatch | |
| 2010/0179663 A1 | 7/2010 | Steinberg | |
| 2010/0185202 A1 | 7/2010 | Lester et al. | |
| 2010/0191244 A1 | 7/2010 | White et al. | |
| 2010/0212138 A1 | 8/2010 | Carroll et al. | |
| 2010/0217109 A1 | 8/2010 | Belcher | |
| 2010/0217270 A1 | 8/2010 | Polinski et al. | |
| 2010/0217336 A1 | 8/2010 | Crawford et al. | |
| 2010/0217338 A1 | 8/2010 | Carroll et al. | |
| 2010/0228257 A1 | 9/2010 | Bonutti | |
| 2010/0249657 A1 | 9/2010 | Nycz et al. | |
| 2010/0249796 A1 | 9/2010 | Nycz | |
| 2010/0262150 A1 | 10/2010 | Lian | |
| 2010/0274253 A1 | 10/2010 | Ure | |
| 2010/0281678 A1 | 11/2010 | Burdulis, Jr. et al. | |
| 2010/0286700 A1 | 11/2010 | Snider et al. | |
| 2010/0292743 A1 | 11/2010 | Singhal et al. | |
| 2010/0305574 A1 | 12/2010 | Fitz et al. | |
| 2010/0318088 A1 | 12/2010 | Warne et al. | |
| 2010/0324692 A1 | 12/2010 | Uthgenannt et al. | |
| 2011/0004317 A1 | 1/2011 | Hacking et al. | |
| 2011/0009869 A1 | 1/2011 | Marino et al. | |
| 2011/0015636 A1 | 1/2011 | Katrana et al. | |
| 2011/0015639 A1 | 1/2011 | Metzger et al. | |
| 2011/0015752 A1 | 1/2011 | Meridew | |
| 2011/0022049 A1 | 1/2011 | Huebner et al. | |
| 2011/0029091 A1 | 2/2011 | Bojarski et al. | |
| 2011/0029116 A1 | 2/2011 | Jordan et al. | |
| 2011/0035012 A1 | 2/2011 | Linares | |
| 2011/0040303 A1 | 2/2011 | Iannotti | |
| 2011/0040334 A1 | 2/2011 | Kaes et al. | |
| 2011/0046735 A1 | 2/2011 | Metzger et al. | |
| 2011/0054478 A1 | 3/2011 | Vanasse et al. | |
| 2011/0066193 A1 | 3/2011 | Lang et al. | |
| 2011/0066245 A1 | 3/2011 | Lang et al. | |
| 2011/0071528 A1 | 3/2011 | Carson | |
| 2011/0071529 A1 | 3/2011 | Carson | |
| 2011/0071530 A1 | 3/2011 | Carson | |
| 2011/0071532 A1 | 3/2011 | Carson | |
| 2011/0071533 A1 | 3/2011 | Metzger et al. | |
| 2011/0092804 A1 | 4/2011 | Schoenefeld et al. | |
| 2011/0093086 A1 | 4/2011 | Witt et al. | |
| 2011/0106254 A1 | 5/2011 | Abel et al. | |
| 2011/0125264 A1 | 5/2011 | Bagga et al. | |
| 2011/0151027 A1 | 6/2011 | Clineff et al. | |
| 2011/0151259 A1 | 6/2011 | Jarman-Smith et al. | |
| 2011/0153025 A1 | 6/2011 | McMinn | |
| 2011/0160736 A1 | 6/2011 | Meridew et al. | |
| 2011/0160867 A1 | 6/2011 | Meridew et al. | |
| 2011/0166578 A1 | 7/2011 | Stone et al. | |
| 2011/0172672 A1 | 7/2011 | Dubeau et al. | |
| 2011/0184419 A1 | 7/2011 | Meridew et al. | |
| 2011/0190899 A1 | 8/2011 | Pierce et al. | |
| 2011/0190901 A1 | 8/2011 | Weissberg et al. | |
| 2011/0213376 A1 | 9/2011 | Maxson et al. | |
| 2011/0214279 A1 | 9/2011 | Park et al. | |
| 2011/0218545 A1 | 9/2011 | Catanzarite et al. | |
| 2011/0224674 A1 | 9/2011 | White et al. | |
| 2011/0251617 A1 | 10/2011 | Ammann et al. | |
| 2011/0269100 A1 | 11/2011 | Furrer et al. | |
| 2012/0010619 A1 | 1/2012 | Barsoum | |
| 2012/0010710 A1 | 1/2012 | Frigg | |
| 2012/0010711 A1 | 1/2012 | Antonyshyn et al. | |
| 2012/0215225 A1 | 8/2012 | Philippon et al. | |
| 2012/0232596 A1 | 9/2012 | Ribeiro | |
| 2012/0271314 A1 | 10/2012 | Stemniski et al. | |
| 2012/0289965 A1 | 11/2012 | Gelaude et al. | |
| 2012/0296339 A1 | 11/2012 | Iannotti et al. | |
| 2012/0303033 A1 | 11/2012 | Weiner et al. | |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| DE | 102009028503 A1 | 2/2011 |
| EP | 0114505 A1 | 8/1984 |
| EP | 0326768 A2 | 8/1989 |
| EP | 0579868 A2 | 1/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1832239 A1 | 9/2007 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| GB | 2447702 A | 9/2008 |
| JP | 59157715 A | 9/1984 |
| JP | 60231208 A | 11/1985 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A2 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |

| | | |
|---|---|---|
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096557 A2 | 8/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A1 | 4/2011 |
| WO | WO-2011106711 A1 | 9/2011 |
| WO | WO-2011109260 A1 | 9/2011 |
| WO | WO-2012006444 A2 | 1/2012 |
| WO | WO-2012061042 A1 | 5/2012 |
| WO | WO-2012173929 A1 | 12/2012 |

OTHER PUBLICATIONS

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

International Preliminary Report on Patentability for PCT/US2010/050701 mailed Apr. 12, 2012 claiming benefit of U.S. Appl. No. 12/571,969, filed Oct. 1, 2009.

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D-computertomographischen Subtraktionverfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

"Amazing Precision. Beautiful Results. The next evolution of MAKOplasty® is here," brochure. (Feb. 2009) MAKO Surgical Corp. 6 pages.

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (2003) pp. 1-8 (12 sheets).

"Patient Matched PMI Implants, C.A.M.R.A. 3-D Imaging," brochure, Biomet, Inc. (1990) 6 pages.

"Regenerex® Tibial Cone Augment, Surgical Technique Addendum to the Vanguard® SSK Revision System," brochure. Biomet® Orthopedics. (2009) pp. 1-8 (12 sheets).

"Signature™ Personalized Patient Care, Surgical Technique Addendum to the Vanguard Knee System" brochure. Biomet® Orthopedics, Inc. (2009) pp. 1-8.

"TruMatch™ Personalized knee replacement solutions," tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics, (2010) pp. 1-25.

"Zimmer® UniSpacer® Knee System," brochure. (2005) Zimmer, Inc. 4 sheets.

Birnbaum, Klaus, M.D., "Computer-Assisted Orthopedic Surgery With Individual Templates and Comparison to Conventional Method," Spine vol. 26, No. 4, pp. 365-370 (2001) Lippincott Williams & Wilkins, Inc.

Botha, Cheri P., Technical Report: DeVIDE—The Delft Visualisation and Image processing Development Environment, pp. 1-49 (May 31, 2006).

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.

Haaker, R.G., et al., "Minimal-invasive navigiert implantierte unikondyläre Knieendoprothese," Orthopäde 2006 35:1073-1079 (2006) Spinger Medizin Verlag.

Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.

Hazen, Eric J., M.D., "Computer-Assisted Orthopaedic Sugery, A New Paradigm," Techniques in Orthopaedics® vol. 18, No. 2, (2003) pp. 221-229.

Hutmacher, Dietmar, W., "Scaffolds in tissue engineering bone and cartilage," Biomaterials, 2000 Elsevier Science Ltd. (pp. 2529-2543).

International Preliminary Report on Patentability and Written Opinion for PCT/US2009/039578 mailed Oct. 28, 2010 claiming benefit of U.S. Appl. No. 12/103,834, filed Apr. 16, 2008.

International Preliminary Report on Patentability and Written Opinion mailed Oct. 28, 2010 for PCT/US2009/039507 claiming benefit of U.S. Appl. No. 12/103,824, filed Apr. 16, 2008.

International Preliminary Report on Patentability for PCT/US2007/013223 mailed Dec. 24, 2008 claiming benefit of U.S. Appl. No. 11/756,057, filed May 31, 2007.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion for PCT/US2007/013223 mailed Nov. 26, 2007, claiming benefit of U.S. Appl. No. 11/756,057, filed May 31, 2007.

International Search Report and Written Opinion for PCT/US2009/039507 mailed Jul. 14, 2009, claiming benefit of U.S. Appl. No. 12/103,824.

International Search Report and Written Opinion for PCT/US2009/056670 mailed Mar. 2, 2010 claiming benefit of U.S. Appl. No. 12/211,407, filed Sep. 16, 2008.

International Search Report and Written Opinion mailed Apr. 22, 2010 for PCT/US2010/024579 claiming benefit of U.S. Appl. No. 12/389,930, filed Feb. 20, 2009.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jul. 31, 2009 for PCT/US2009/039578 claiming benefit of U.S. Appl. No. 12/103,834, filed Apr. 16, 2008.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty." The Journal of Bone & Joint Surgery(2009) pp. 153-158. vol. 91-A, Supplement 1.

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Murphy, S.B., et al. "The Hip Sextant: Navigation of Acetabular Component Orientation Using a Mechanical Instrument," brochure. (2009) 1 page.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&Issue . . . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

International Search Report and Written Opinion mailed Nov. 15, 2012, for PCT/US2012/052853, which claims benefit of U.S. Appl. No. 13/221,968, filed Aug. 31, 2011.

International Search Report and Written Opinion mailed Dec. 18, 2012 for PCT/US2012/059189, which claims benefit of U.S. Appl. No. 13/597,478, filed Aug. 29, 2011.

\* cited by examiner

PATIENT-MODIFIED IMPLANT

CROSS-REFERENCE TO RELATED APPLICATIONS

This application is a divisional of U.S. application Ser. No. 12/103,834, filed Apr. 16, 2008, which claims the benefit of U.S. Provisional Application No. 60/912,178, filed on Apr. 17, 2007, and which is related to U.S. application Ser. No. 11/756,057, filed on May 31, 2007, which claims the benefit of U.S. Provisional Application No. 60/812,694, filed on Jun. 9, 2006.

The disclosures of the above applications are incorporated herein by reference.

INTRODUCTION

Various custom made, patient-specific orthopedic implants and associated templates and guides are known in the art. Such implants and guides can be developed using commercially available software. Custom guides are used to accurately place pins, guide bone cuts, and insert implants during orthopedic procedures. The guides are made from a preoperative plan formed from an MRI or CT scan of the patient and rely on matching an anatomic feature for correct positioning.

The present teachings provide semi-custom implants that can reduce inventory and allow more accurate placement and additional flexibility in addressing diverse patient-specific requirements.

SUMMARY

The present teachings provide an orthopedic implant. The implant has a first portion including at least one patient-adjustable feature, and a second portion including at least one standard feature.

The present teachings also provide an orthopedic implant manufacturing method. The method includes preparing a three-dimensional image of a patient's joint, selecting a standard size implant closely matching the joint, and modifying at least one feature of the implant to be patient-specific.

In another aspect, the implant is a femoral implant, and the method includes modifying a plurality of features of the femoral implant to be patient-specific.

The present teachings also provide an orthopedic implant that includes a first portion including at least one feature modified to be patient-specific and match the anatomy of a specific patient from a three-dimensional digital image of a patient's joint using computer modeling. The orthopedic implant includes a non-custom inner bone-engaging surface including a plurality of planar surfaces configured for engagement with non-custom bone cuts.

The present teachings provide an orthopedic implant that includes a non-custom inner bone-engaging surface including a plurality of planar surfaces configured for engagement with standard size femoral bone cuts prepared for a non-custom femoral implant. In some embodiments, the orthopedic implant includes a patient-specific feature, such as an anterior femoral flange of the orthopedic implant configured during a preoperative plan to have a patient-specific shape and closely match a corresponding portion of a femur of a specific patient from a three-dimensional digital image of a patient's joint using computer modeling. The patient-specific shape of the anterior femoral flange of the orthopedic implant is obtained by modifying a digital image of the non-custom femoral implant without modifying the plurality of planar surface of the inner bone-engaging surface. In some embodiments, the patient-specific feature is the orientation or the depth of a patella track.

The present teachings provide an orthopedic implant that includes a non-custom tibial bearing component, and a tibial tray including a non-custom locking mechanism couplable with the non-custom tibial bearing. The tibial tray has a patient-specific profile configured during a preoperative plan to be patient-specific and closely match a corresponding profile of a tibia of a specific patient from a three-dimensional digital image of a patient's joint using computer modeling, wherein the patient-specific profile of the tibial tray is obtained by modifying a digital image of a non-custom tibial implant without modifying the non-custom locking mechanism.

Further areas of applicability of the present teachings will become apparent from the description provided hereinafter. It should be understood that the description and specific examples are intended for purposes of illustration only and are not intended to limit the scope of the teachings.

BRIEF DESCRIPTION OF THE DRAWINGS

The present teachings will become more fully understood from the detailed description and the accompanying drawings, wherein.

DESCRIPTION OF VARIOUS EMBODIMENTS

Figure 1:
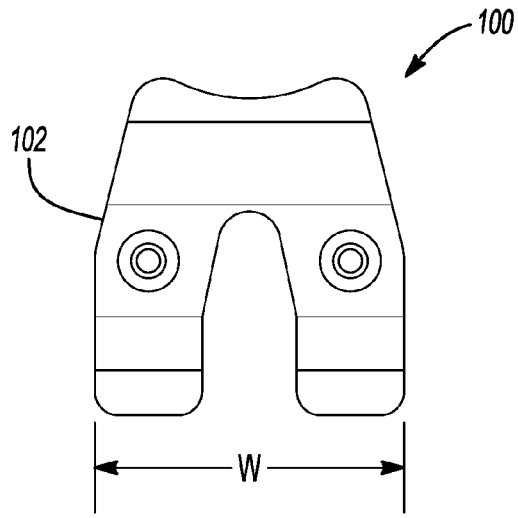
FIG. 1 is a plan view of an exemplary femoral implant according to the present teachings.

The following description is merely exemplary in nature and is in no way intended to limit the teachings, its application, or uses. For example, although the present teachings are illustrated for specific implants and alignment guides in hip or knee surgery, the present teachings can be used with other implants and guides, templates, jigs, drills, rasps or other instruments used in various orthopedic procedures.

The present teachings generally provide a surgery system for use in orthopedic surgery for the knee, hip, or shoulder, for example. The surgery system can include various implant components 100, patient-specific alignment guides or templates 600, and cutting blocks or other conventional instruments 610, 620 that can be used in the specific orthopedic procedure. At least one implant component 100 can be semi-custom made. The semi-custom implant components are standard size components that have at least one feature modified to match a specific patient, as discussed below.

The alignment guides 600 can be used either with conventional (standard size) or patient-specific femoral and tibial prosthesis components prepared with computer-assisted image methods. The implant components 100 can be patient-specific (custom made) or semi-custom. Computer modeling for obtaining three dimensional images of the patient's anatomy using MRI or CT scans of the patient's anatomy, the semi-custom and/or custom made implant components 100, and the patient-specific alignment guides 600 can be provided by various CAD programs and/or software available, for example, by Materialise USA, Ann Arbor, Mich.

The alignment guides 600 can be generally formed using computer modeling for matching a three-dimensional image of the patient's bone surface (with or without the cartilage) by known methods. Further details of patient-specific alignment guides and associated methods are disclosed in U.S. application Ser. No. 11/756,057, filed on May 31, 2007, the disclosure of which is incorporated herein by reference.

Similarly, the implant components can be selected and modified to include patient-specific features by using computer modeling of the joint, as described above. A set of conventional femoral knee implants can be modeled and overlaid over the CAD image data to first determine the closest fit based on standard sizes. These standard sized overlays or templates can be based on commercially available implant systems, such as, for example, the Vanguard Knee System, commercially available from Biomet, Inc, of Warsaw, Ind., in size increments of 2.5 mm. Using standard sized implants as a base for semi-custom implant components can allow standard instrument sets to be used depending on the specific size selected. After the overlay is positioned on the digital representation of the femur, various adjustments can be made to this femoral implant.

Figure 2:
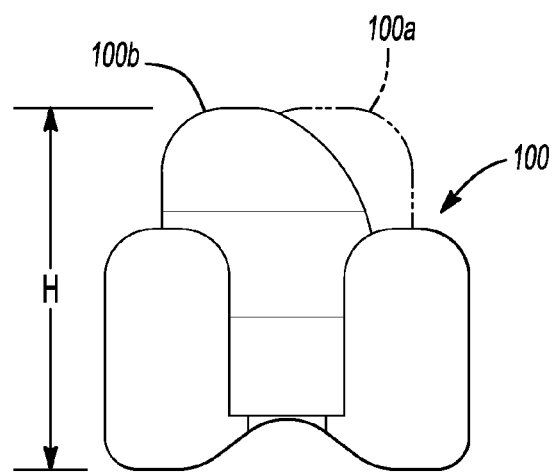
FIG. 2 is a posterior elevated view of the femoral implant of FIG. 1.
Figure 3:
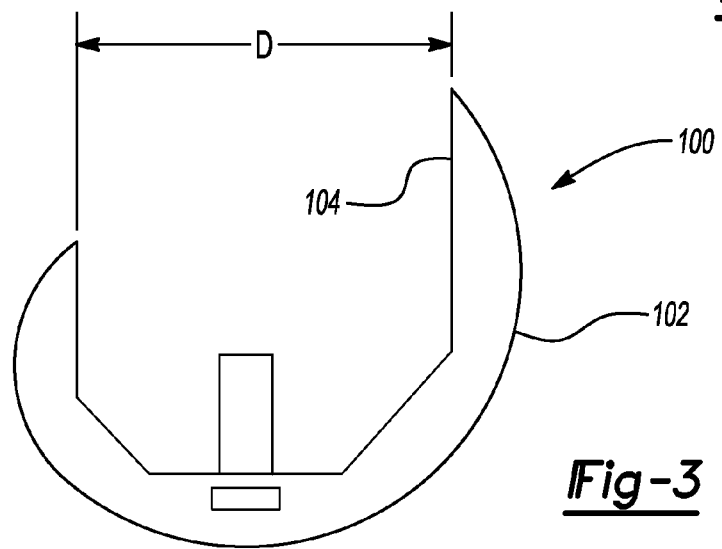
FIG. 3 is an anterior-posterior sectional view of the femoral implant of FIG. 1.

Referring to FIGS. 1-3, various views of an exemplary semi-custom implant component 100 in the form of a femoral component for a knee replacement surgery system are illustrated. The semi-custom implant component 100 can include certain portions that are custom-made to match a particular patient using imaging techniques, and other portions that are provided in a series of standardized size increments to ensure a good fit. For example, the outside geometry of the femoral component 100 can be patient-specific or patient-matched. As an illustration, the width W and height H, and/or optionally the shape and dimensions of the entire articulating or outer surface 102, or portions thereof, can match/conform with that of the patient's corresponding joint surface. The inside geometry of the femoral component 100, such as the bone-engaging inner surface 104, can be selected from a standardized series of sizes, thereby allowing the use of standard instruments, such as cutting guides and resection instruments, to be used with the semi-custom implant components 100, and avoiding the need for specialized instruments and associated manufacturing and training costs.

With continued reference to FIGS. 1-3, to obtain a good match, the difference between consecutive sizes in the inner anterior-posterior distance D can be 3 mm or less to allow for as good a fit between the implant component 100 and the joint surface without the need to match or conform the inner surface 104 to the patient. In other words, the semi-custom implant component 100 is an implant component that can include certain portions, including shapes, dimensions, and/or sizes that are custom-made for a particular patient, while other portions including shapes and/or dimensions of the component are provided in a series of standardized sizes in increments that can provide a good fit without being fully custom-made to a particular patient.

Figure 8:
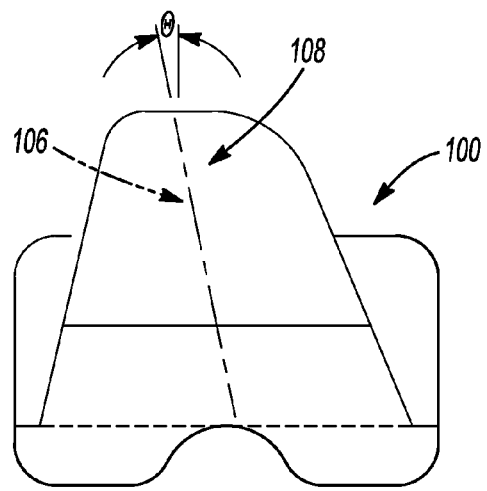
FIG. 8 is an anterior elevated view of a femoral implant according to the present teachings.
Figure 9:
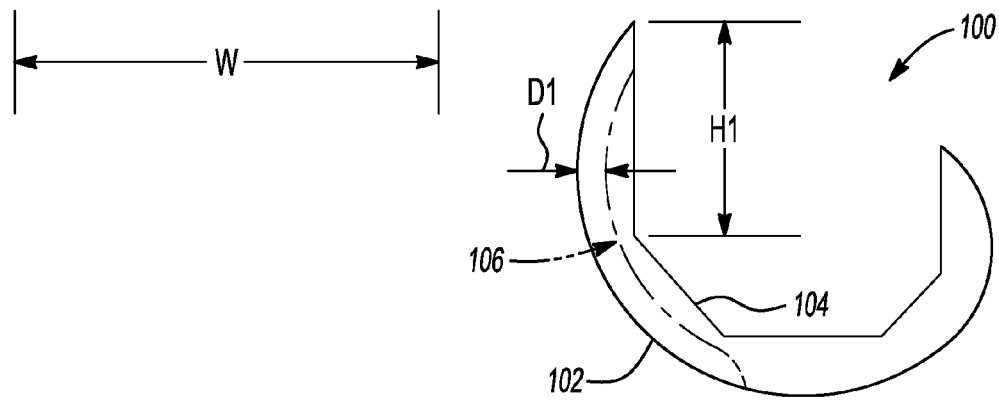
FIG. 9 is an anterior-posterior sectional view of the femoral implant of FIG. 8.

In another aspect, and referring to the exemplary illustrations of FIGS. 8 and 9, five adjustments can be made to a standard size femoral component to obtain a semi-custom femoral implant component 100. These five adjustments can include the medial/lateral width W, the angle 8 of the patella track 106, the depth D1 of the patella track, the shape of the anterior flange 108, such as right or left-sided and a height of the anterior flange, such as the height H1 shown in FIG. 9, or overall height H, shown in FIG. 2. These five features or parameters can be adjusted to more closely match the knee of the patient without requiring changes in the standard cuts for the selected standard knee implant, because the bone engaging inner surface 104 does not substantially change allowing standard cutting guides and resections instruments corresponding to standard sizes to be used. This modified or patient matched digital model of the semi-custom implant can then be provided to the surgeon along with the image data for review. The surgeon can confirm whether the proposed design is acceptable, and the specific patient matched implant can be manufactured from the digital model.

Figure 10:
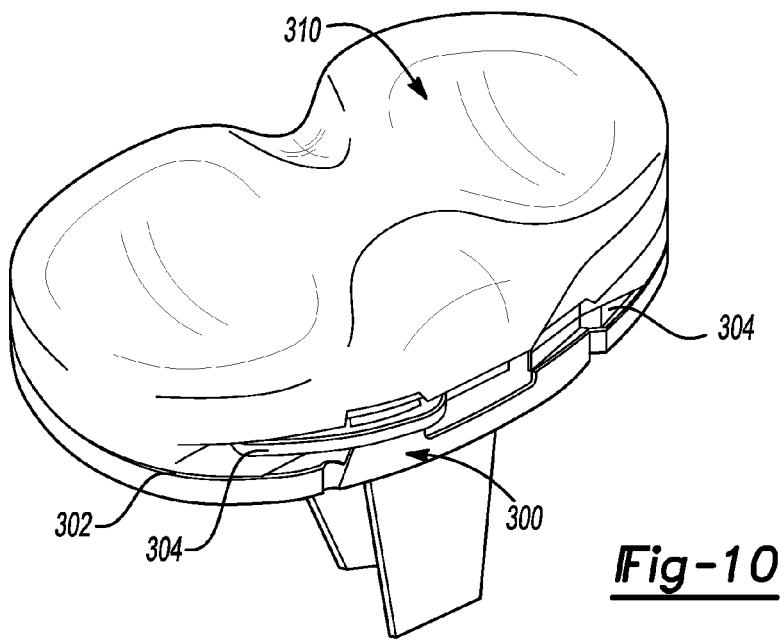
FIG. 10 is a perspective view of a tibial component according to the present teachings.

The surgery system can include patient-specific and/or conventional (standard size) implants for the remaining components of the knee replacement system, such as the tibial component, bearing component and patella component. For example, and referring to FIG. 10, a tibial component 300 can be designed with a profile 302 that matches and conforms to the patient's anatomy based on the 3-D image data of the patient's bone. The resulting tibial component 300 can still have standard features, including a standard locking mechanism for bearings, such as, for example, slots 304 for coupling with a standard bearing component 310. The standard locking mechanism allows existing inventory of bearings to be used. In another aspect, the bearing components 310 can be similarly customized.

In another aspect, the tibial component 300 can also be designed in closely packed tibial sizes that very in increments of less that 2 mm in width and are available for manufacture on as-needed basis. When used with patient-specific alignment guides made from digital images of the joint, the closely packed sizes need not be stocked in inventory, but manufactured only in the size determined from the digital image from planned molds or other just-in-time manufacturing methods.

In another aspect, disease-specific off-the shelf implants can be provided and included in a surgery kit. Each disease-specific implant can be designed to address a specific deformity, by making angle or size adjustment related to the deformity, such as different lengths or thickness or angles of certain portions of the implant component, such as the size and shape of femoral condyles, the patella track angle, etc. Each disease-specific implant can be used for multiple patients with the same deformity/disease, such as valgus, varus or flexion deformities. In this regard, for each patient with the same deformity, one or more off-the-shelf disease-specific implants can be selected to address the patient's needs without using patient-specific implants.

Figure 4:
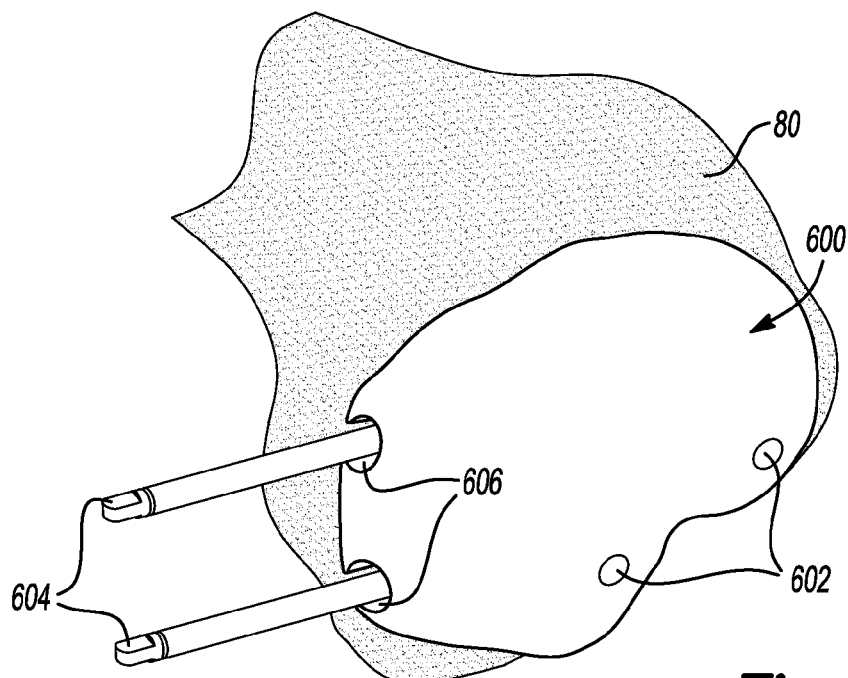
FIG. 4 is an environmental view illustrating an exemplary femoral alignment guide according to the present teachings.
Figure 5:
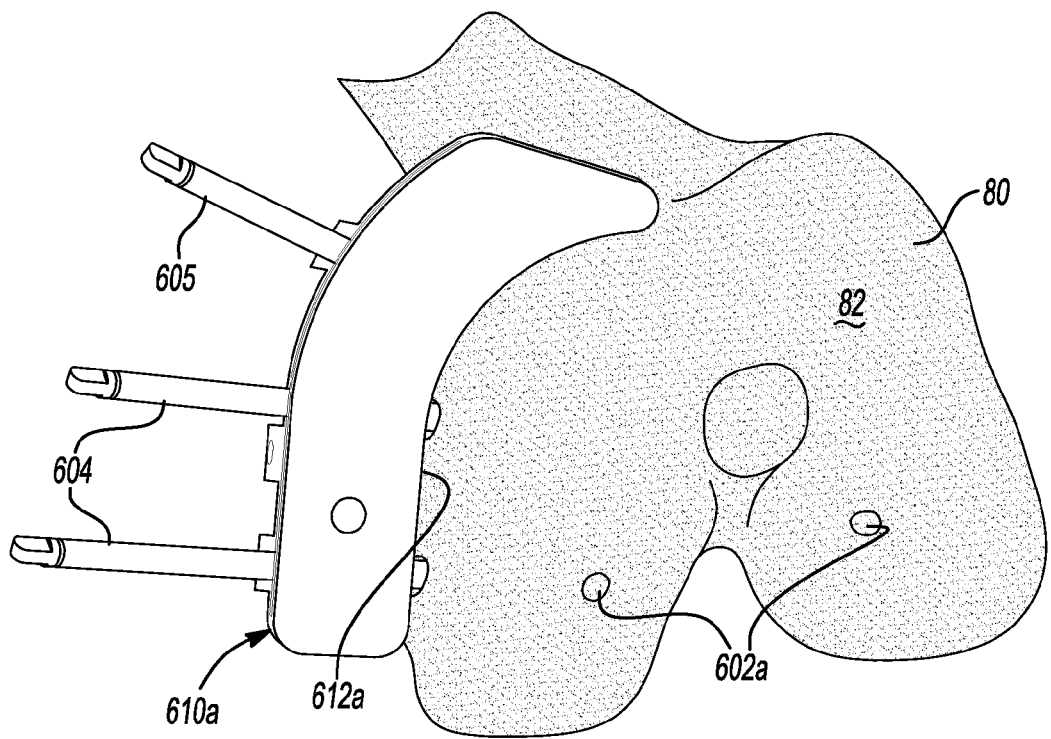
FIG. 5 is an environmental view illustrating an exemplary distal cutting block according to the present teachings.
Figure 6:
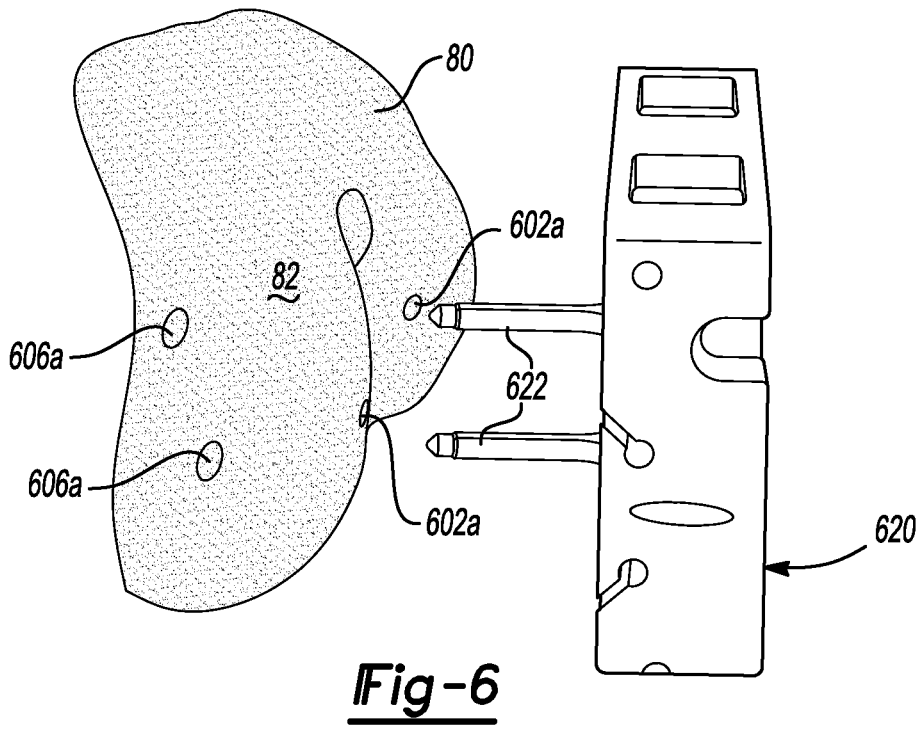
FIG. 6 is an environmental view illustrating an exemplary four-in-one cutting block according to the present teachings.

The surgery system can also include patient-specific alignment guides 600, as illustrated in FIG. 4 for a joint surface 82 of the distal femur 80. The patient specific alignment guide 600 can define openings 606 for guide elements 604 that pass through corresponding holes 606a drilled in the femur, and openings 602 for drilling holes 602a on the femur 80, as shown in FIGS. 4, and 6. The surgery system can also include a set of cutting blocks for the femoral joint surface 82, such as the distal cutting block 610 illustrated in FIG. 5 and mounted on the femur 80 with various guide or fixation elements 604, 605, and the four-in-one cutting block 620 illustrated in FIG. 6. The four-in-one cutting block 620 can be supported on the femur with pins 622 received in openings 602a. Other cutting blocks, drill guides or other instruments can also be used. The joint surface 82 can be a bone surface with or without soft tissue, such as articular cartilage for the knee or other joint soft tissue. It will be appreciated that other instruments, such as drill guides, guide pins, attachment pins or pegs or others can be included in the surgery system.

Figure 7:
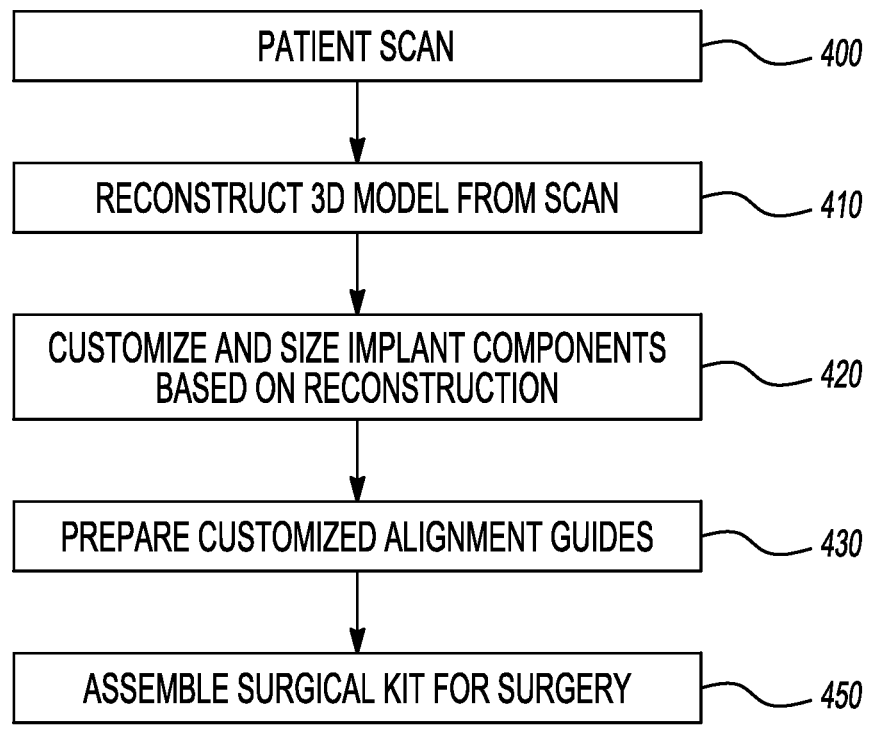
FIG. 7 is a flowchart of an exemplary method according to the present teachings.

The surgery system can be used for surgical pre-planning as illustrated in FIG. 7. The patient's knee, or other joint, can be scanned using an imaging technique, such as MRI or CT, at 400. A three-dimensional (3D) model of the joint surfaces can be reconstructed at 410 using known computer imaging methods. The implant components 100 can be designed, sized and positioned using the 3D reconstruction, at 420. As discussed above, the implant components 100 can include conventional, custom made, or semi-custom implant components 100. The semi-custom implant components can include some portions that are of standard sizes, such as a bone-engaging inner surface 104 (shown with five planar surfaces in FIG. 9), and other portions that are customized for the patient, including portions of the articulating surface or other outer dimensions and orientations of the articulating surface 102 of the implant 100. Customized alignment guides 600 for the joint surfaces, such as femoral and tibial alignment guides 600 for a total knee replacement, can be designed and prepared based on the 3D reconstruction and the implants 100, at 430. A surgery system or kit can be assembled for the surgeon at the time of surgery, at 450. The surgery system can include at least one semi-custom implant component 100, at least one patient specific alignment guide 600, and at least one cutting block 610.

It will be appreciated that surgery kits as described above can be constructed for various joints, including the knee, the hip, the shoulder, etc. The present teachings provide the ability to customize implant and alignment guide components and their position using patient-specific data. Further, the amount of inventory required in the operating room can be reduced because the sizes of the various semi-custom implant components 100 are known prior to surgery and only the required size is sent to the surgeon for the surgical procedure. In another aspect, when close-packed sizes are planned, the small difference between individual sizes of the implant components 100, such as 3 mm or 2.5 mm or less, can allow optimal anterior-posterior fit to the joint surface 80 without adverse impact on inventory requirements, because only the required size can be manufactured and shipped for a specific patient based on the patient's image data. Additionally, the use of semi-custom implant components based on anterior-posterior sizing, as contrasted to fully patient-specific components, allows use and re-use of standard cutting blocks. Disposable cutting blocks can also be mass produced in high volumes at less cost because of the standardization.

The foregoing discussion discloses and describes merely exemplary arrangements of the present teachings. One skilled in the art will readily recognize from such discussion, and from the accompanying drawings that various changes, modifications and variations can be made therein without departing from the spirit and scope of the teachings as described herein.

What is claimed is:

1. A method for manufacturing an orthopedic implant, comprising:
    constructing a three-dimensional digital image of a patient's joint using computer modeling;
    obtaining a digital image of a femoral implant having a non-custom inner bone-engaging surface including a plurality of planar surfaces configured for engagement with standard size femoral bone cuts prepared for a non-custom femoral implant;
    modifying the digital image of the femoral implant by configuring an anterior femoral flange of the femoral implant to have a patient-specific shape and size and to closely match a corresponding portion of a femur of a specific patient based on the three-dimensional image of the patient's joint; and
    manufacturing the femoral implant based on the digital image.

2. The method of claim 1, further comprising modifying the digital image of the femoral implant by configuring the anterior flange of the femoral implant to have a patient-specific height that is based on the three-dimensional image of the patient's joint.

3. The method of claim 1, wherein obtaining the digital image of the femoral implant includes creating the digital image.

4. The method of claim 1, wherein obtaining the digital image of the femoral implant includes selecting the femoral implant from a plurality of femoral implants having different non-custom sizes based on a size of the patient's joint.

5. The method of claim 1, further comprising overlaying the digital image of the femoral implant on the three-dimensional image of the patient's joint.

6. A method for manufacturing an orthopedic implant, comprising:
    constructing a three-dimensional digital image of a patient's joint using computer modeling;
    obtaining a digital image of a femoral implant having a non-custom inner bone-engaging surface including a plurality of planar surfaces configured for engagement with standard size femoral bone cuts prepared for a non-custom femoral implant;
    modifying the digital image of the femoral implant by configuring an orientation of a patella track of the femoral implant to have a patient-specific shape and size and to closely match a corresponding portion of a femur of a specific patient based on the three-dimensional image of the patient's joint; and
    manufacturing the femoral implant based on the digital image.

7. The method of claim 6, further comprising modifying the digital image of the femoral implant by configuring the patella track of the femoral implant to be oriented at a patient-specific angle with respect to a medial/lateral centerline of the orthopedic implant based on the three-dimensional image of the patient's joint.

8. The method of claim 6, wherein obtaining the digital image of the femoral implant includes creating the digital image.

9. The method of claim 6, wherein obtaining the digital image of the femoral implant includes selecting the femoral implant from a plurality of femoral implants having different non-custom sizes based on a size of the patient's joint.

10. The method of claim 6, further comprising overlaying the digital image of the femoral implant on the three-dimensional image of the patient's joint.

11. A method for manufacturing an orthopedic implant, comprising:
    constructing a three-dimensional digital image of a patient's joint using computer modeling;
    obtaining a digital image of a femoral implant having a non-custom inner bone-engaging surface including a plurality of planar surfaces configured for engagement with standard size femoral bone cuts prepared for a non-custom femoral implant;

modifying the digital image of the femoral implant by configuring a depth of a patella track of the femoral implant to have a patient-specific shape and size and to closely match a corresponding portion of a femur of a specific patient based on the three-dimensional image of the patient's joint; and manufacturing the femoral implant based on the digital image.

12. The method of claim 11, wherein obtaining the digital image of the femoral implant includes creating the digital image.

13. The method of claim 11, wherein obtaining the digital image of the femoral implant includes selecting the femoral implant from a plurality of femoral implants having different non-custom sizes based on a size of the patient's joint.

14. The method of claim 11, further comprising overlaying the digital image of the femoral implant on the three-dimensional image of the patient's joint.

15. A method for manufacturing an orthopedic implant, comprising:

constructing a three-dimensional digital image of a patient's joint using computer modeling;

obtaining a digital image of a tibial tray including a non-custom locking mechanism couplable with a non-custom tibial bearing;

modifying the digital image of the tibial tray by configuring a peripheral surface of the tibial tray to be patient-specific and to closely match a corresponding peripheral surface of a tibia of a specific patient based on the three-dimensional digital image of the patient's joint; and manufacturing the tibial tray based on the digital image.

16. The method of claim 15, wherein obtaining the digital image of the tibial tray includes creating the digital image.

17. The method of claim 15, wherein obtaining the digital image of the tibial tray includes selecting the tibial tray from a plurality of tibial trays having different non-custom sizes based on a size of the patient's joint.

18. The method of claim 15, further comprising overlaying the digital image of the tibial tray on the three-dimensional image of the patient's joint.

19. The method of claim 15, wherein the non-custom locking mechanism includes a plurality of recesses on the tibial tray.

20. The method of claim 15, further comprising:

obtaining a digital image of a tibial bearing couplable with the locking mechanism of the tibial tray;

modifying the digital image of the tibial bearing by configuring a peripheral surface of the tibial bearing to be patient-specific and to closely match a corresponding peripheral surface of the tibia of the specific patient based on the three-dimensional digital image of the patient's joint; and manufacturing the tibial bearing based on the digital image of the tibial bearing.

* * * * *